United States Patent [19]
Goettsche et al.

[11] Patent Number: 4,908,362
[45] Date of Patent: Mar. 13, 1990

[54] SALT OF A SUBSTITUTED MORPHOLINE WITH FLUOBORIC ACID, FUNGICIDAL COMPOSITION AND USE

[75] Inventors: Reimer Goettsche, Baden-Baden; Hans-Norbert Marx, Buehl-Weitenung, both of Fed. Rep. of Germany

[73] Assignee: Dr. Wolman GmbH, Sinzheim, Fed. Rep. of Germany

[21] Appl. No.: 12,376

[22] Filed: Feb. 9, 1987

[30] Foreign Application Priority Data

Feb. 18, 1986 [DE] Fed. Rep. of Germany ....... 3605007

[51] Int. Cl.$^4$ .................... A01N 43/84; C07D 265/30
[52] U.S. Cl. .................... 514/231.2; 544/107
[58] Field of Search .................... 544/107; 514/231.2

[56] References Cited

U.S. PATENT DOCUMENTS 3,686,399  8/1972  Sanne .................... 514/231.2
4,567,277  1/1986  Marx et al. .................... 548/306

*Primary Examiner*—Robert W. Ramsuer
*Attorney, Agent, or Firm*—Oblon, Spivak, McClelland, Maier & Neustadt

[57] ABSTRACT

The salt of N-tridecyl-2,6-dimethylmorpholine with fluoboric acid, and fungicides, insecticides and wood preservatives containing this salt.

4 Claims, No Drawings

SALT OF A SUBSTITUTED MORPHOLINE WITH FLUOBORIC ACID, FUNGICIDAL COMPOSITION AND USE

The present invention relates to the novel salt of N-tridecyl-2,6-dimethylmorpholine with fluoboric acid

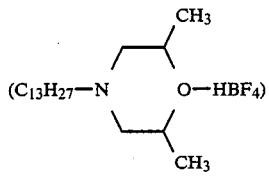

and its uses as a fungicide, in particular for preserving wood.

It has been disclosed that N-tridecyl-2,6-dimethylmorpholine (tridemorph) can be used as a fungicide (DE 1 164 152). However, the compound has no effect on insects.

It has also been disclosed that the salt of 2-(methoxycarbonylamino)-benzimidazole with fluoboric acid can be used as a fungicide in wood preservation (DE 3 138 575.3). The fluoboric acid constitutes an additional fungicidal active ingredient introduced into the benzimidazole derivative.

It is also known that water-soluble salts of fluoboric acid can be reached with alkali metal dichromates in the wood and that the wood can be preserved in this way. These salts are available commercially as CFB salts.

The water-soluble salts of fluoboric acid are not fixed in the wood.

They can only be fixed in the wood via chromium cryolite formation (eg. $Na_3CrF_6$), by adding chromates. However, the fixation of fluorine is not complete since the free fluoride ions are formed in the wood from the fluoborates only at a pH above 7, and a substantial excess of chromate is necessary for this purpose. In the conventional salt mixture (about 33% of alkali metal dichromate), more than 50% of the fluorine is washed out with water. Moreover, the salt mixtures require from 2 to 6 weeks for fixing, depending on climatic conditions; during this period, chromium (VI) may be washed out of the wood and may pollute the environment.

We have found that the salt of N-tridecyl-2,6-dimethylmorpholine with fluoboric acid ($HBF_4$) has a very good fungicidal and insecticidal action. It is insoluble in water, but with the aid of ionic or nonionic emulsifiers and with or without the addition of organic solvents it is possible to prepare emulsion concentrates which form clear microemulsions in water. These microemulsions can be introduced into the wood by conventional manual methods (eg. painting, immersion or spraying) or large-scale industrial methods (eg. pressure process or double vacuum process) and provide adequate protection against wood-destroying animals and plants, even in the open, since they are not washed out through the effects of weather.

PREPARATION EXAMPLE 30 g of technical grade N-tridecyl-2,6-dimethylmorpholine is reacted with 8.8 g of fluoboric acid in 26.4 g of water, and the water-insoluble pasty precipitate obtained is filtered off and dried to give 38.5 g of the salt of N-tridecyl-2,6-dimethylmorpholine with fluoboric acid having a melting point of about 30° C.

For example, tridemorph fluoborate can be mixed with organic solvents and nonionic emulsifiers, and the mixture emulsified in water. It is also possible to neutralize a mixture of tridemorph and dimethyl-($C_{10}$-$C_{16}$)alkylamines using fluoboric acid (in an equivalent amount, based on tridemorph, or in excess), with or without the addition of a substituted carboxylic acid, eg. lactic acid, tartaric acid, gluconic acid or adipic acid, and/or phosphoric acid or phosphonic acid, so that the salt of the dimethylalkylamine has an emulsifying effect on the tridemorph fluoborate and forms an aqueous microemulsion with water. The dimethylalkylamine salt may also be added to the tridemorph fluoborate as a mixture with solvents or nonionic emulsifiers. The wood-preserving efficiency of the mixture is further improved by the fungicidal activity of the dimethylalkylamine itself. It is surprising that the novel salt can be emulsified in water in a simple manner, a clear microemulsion being formed.

To improve the corrosion behavior with respect to iron and steel, carboxylic acids, eg. isononanoic acid, isooctanoic acid or p-tert-butylbenzoic acid, may be added.

The Examples which follow illustrate mixtures which can be emulsified in water to give microemulsions.

EXAMPLE 1

20% by weight of tridemorph
6% by weight of fluoboric acid
18% by weight of dipropylene glycol
50% by weight of oxyethylated nonylphenol (9 moles of ethylene oxide per mole of substituted phenol)
6% by weight of water A 10% strength emulsion of the mixture in water can be used, for example, for manual methods.

EXAMPLE 2

20% by weight of tridemorph
31% by weight of dimethyl-$C_{10}$-$C_{16}$-alkylamine mixture
9.% by weight of lactic acid
10% by weight of fluoboric acid (excess)
20% by weight of butyglycol acetate
10% by weight of water A 10% strength emulsion of the mixture in water can be used, for example, for large-scale industrial methods or manual methods.

EXAMPLE 3

20% by weight of tridemorph
33% by weight of a dimethyl-$C_{16}$-alkylamine
12% by weight of phosphoric acid
6% by weight of fluoboric acid
20% by weight of propylene glycol
9% by weight of water A 1.5% strength emulsion of the mixture in water can be used, for example, for large-scale industrial methods.

EXAMPLE 4

20% by weight of tridemorph
30% by weight of a dimethyl-$C_{12}$-alkylamine
10% by weight of oxyethylated nonylphenol (9 moles of ethylene oxide per mole of phenol)
10% by weight of propylene glycol
10% by weight of fluoboric acid
7% by weight of phosphoric acid 1.3% by weight of isooctanoic acid
11.7% by weight of water A 1-10% strength emulsion of the mixture in water can be used for large-scale industrial methods or manual methods.

EXAMPLE 5

20% by weight of tridemorph
30% by weight of a dimethyl-$C_{14}$-alkylamine
20% by weight of propylene glycol
10% by weight of fluoboric acid
5% by weight of gluconic acid
15% by weight of water A 1-10% strength emulsion of the mixture in water can be used for large-scale industrial methods or manual methods.

EXAMPLE 6

20% by weight of tridemorph
35% by weight of a dimethyl-$C_{12}$-$C_{16}$-alkylamine mixture
11.5% by weight of fluoboric acid
22.0% by weight of lactic acid
11.5% by weight of water It is also possible to use other carboxylic acids, eg. citric acid, tartaric acid or adipic acid. However, to prepare the mixtures in a simple manner, it is advisable to use acids which are commercially available in liquid form (eg. 90% strength lactic acid). Such mixtures in the form of solutions are directly obtainable by mixing the individual components. In the case of crystalline acids (as mentioned above), long stirring times are required in order to prepare solutions. The fluoboric acid may also be present in excess; in this case, those regions of the wood which are not accessible to impregnation (heartwood) are protected by diffusion.

It is advisable to bring the pH of the mixture to 2.0-5.0, preferably 3.0-4.0, depending on the amount of acid added and the concentration used.

The mixtures can be colored by means of water-soluble control dyes. Weather-resistant colorations can be produced on the wood by means of water-insoluble dyes which dissolve in the mixtures and are emulsified with these.

We claim:

1. The salt of N-tridecyl-2,6-dimethylmorpholine with fluoboric acid.

2. Fungicide containing a solid or liquid carrier and the salt of N-tridecyl-2,6-dimethylmorpholine with fluoboric acid.

3. A wood preservative containing a solid or liquid carrier and the salt of N-tridecyl-2,6-dimethylmorpholine with fluoboric acid.

4. A method of controlling fungi, wherein the fungi or the materials threatened by fungi attack are treated with the salt of N-tridecyl-2,6-dimethylmorpholine with fluoboric acid.

* * * * *